United States Patent [19]

Minisci et al.

US005175318A

[11] Patent Number: 5,175,318

[45] Date of Patent: Dec. 29, 1992

[54] PROCESS FOR THE PREPARATION OF QUINONES

[75] Inventors: Francesco Minisci; Attilio Citterio; Elena Vismara; Silvia De Bernardinis, all of Milan; Carlo Neri, San Donato Milanese; Luciano Pallini, Fornovo Taro; Mariano Correale, Bonate Sotto, all of Italy

[73] Assignees: Consiglio Nazionale Della Ricerche, Rome; Enicham Synthesis, Palermo; Brichima, S.p.A., Bergano, all of Italy

[21] Appl. No.: 866,108

[22] Filed: Apr. 7, 1992

Related U.S. Application Data

[63] Continuation of Ser. No. 647,199, Jan. 28, 1991, which is a continuation of Ser. No. 60,321, Jun. 10, 1987, abandoned.

[30] Foreign Application Priority Data

Jun. 11, 1986 [IT] Italy ............................. 20754 A/86

[51] Int. Cl.$^5$ ............................................. C07C 50/04
[52] U.S. Cl. .................................... 552/296; 552/297; 552/298; 552/307; 552/308; 552/309
[58] Field of Search ............... 552/296, 297, 298, 307, 552/308, 309

[56] References Cited

U.S. PATENT DOCUMENTS

| 3,297,445 | 1/1967 | Duennebier et al. ................... 96/95 |
| 3,671,552 | 6/1972 | Le Bris et al. .................. 260/396 R |
| 4,482,493 | 11/1984 | Matsumoto ..................... 260/396 R |

FOREIGN PATENT DOCUMENTS 2460361  6/1976  Netherlands .

OTHER PUBLICATIONS

European Search Report.
Chemical Abstracts, vol. 84, 1976, p. 452, Abstract No. 43638r Mitsubishi Petrochemical Co., Ltd.

Primary Examiner—Arthur C. Prescott
Attorney, Agent, or Firm—Birch, Stewart, Kolasch & Birch

[57] ABSTRACT

Phenols are oxidated to quinones with hydrogen peroxide in the presence of catalytic amounts of bromine, iodine, hydrogen bromide and hydrogen iodide.

22 Claims, No Drawings

PROCESS FOR THE PREPARATION OF QUINONES

This application is a continuation, of application Ser. No. 07/647,199 filed on Jan. 28, 1991, which is a continuation of application Ser. No. 07/060,321, filed on Jun. 10, 1987, now abandoned.

The object of the present invention is a novel catalytic a process for the synthesis of quinones. Such process is accomplished by oxidating 2,6-disubstituted phenols or diphenols with $H_2O_2$ in the presence of catalytic amounts of bromine, iodine, hydrogen bromide, or hydrogen iodide: the catalytic oxidation which is thus accomplished is extremely simple, low cost and highly selective.

Quinones are known to be an important class of compounds of the chemical industry. For example, it is known that 1,4-benzoquinone is used in the photographic industry and in the industry of dyes; both 1,4-naphthoquinone and 9.10-anthraquinone are used in the industry of dyes, 2-methylnaphthoquinone is a commercial Vitamin K, and 2,3,5-trimethyl-1,4-benzoquinone is an intermediate for the synthesis of vitamins, etc. (D. H. Barton "Comprehensive Organic Chemistry", Vol. 1, page 1,213, 1979). Furthermore, insofar as the quinones can be easily hydrogenated to yield diphenol compounds which are also industrially useful particularly in the photographic fields and in the field of antioxidants, these compounds may be conveniently obtained by starting from quinones, which in turn are obtained by starting from mono-phenols diphenol compounds are easily accessible products.

A general method for the synthesis of quinones comprises the oxidation of phenols and diphenols with various oxidants, such as $CrO_3$, $Ag_2O$, $Ag_2CO_3$, $Ce^{IV}$ salts, the Fremy salt $(KO_3S)_2NO$, $(PhSeO)_2O$ and so forth. However, the use of these oxidants has serious drawbacks from an industrial viewpoint, such as, e.g., high costs (this is the case of the salts of Ag, Ce, of the Fremy salt, of selenium derivatives, etc.), or large amounts of salts to be disposed of (chrome salts), or highly toxic substances (selenium oxides).

The use of hydrogen peroxide with different catalysts in the oxidation of phenols, generally leads to the corresponding 1,2- and 1,4-diphenols (see, e.g., the German patent application No. 2,162,552, C.A. 86 189487d, C.A. 94 191302y and C.A. 85 139662d). A method is known as well for the oxidation of phenols to quinones, which uses hydrogen peroxide, but which is carried out in two steps, and provides first the synthesis of the analogous 4-chloro derivative, by means of the treatment of the phenol with HCl and $H_2O_2$ followed, in a second step, by the oxidation of this intermediate with $H_2O_2$ in acetic acid, to yield the quinone (see C.A. 85, 94070c).

The present inventors have found now, and this is the object of the present patent application, that it is possible to catalytically oxidate, in an extremely simple, convenient and selective way, a 2,6-disubstituted phenol or diphenol with $H_2O_2$ in the presence of a catalyst selected from bromine, iodine, hydrogen bromide and hydrogen iodide, to yield the corresponding quinone. The reaction is generally applicable to 2,6-disubstituted mono-phenols, of both mono-, and di- and tri-cyclic structure, as well as to 1,2- and 1,4-diphenols. However, in view of the industrial interest of the end product, a preferred group of phenol starting products, which can be advantageously oxidated to the corresponding quinones, comprises those phenols of general formula (I):

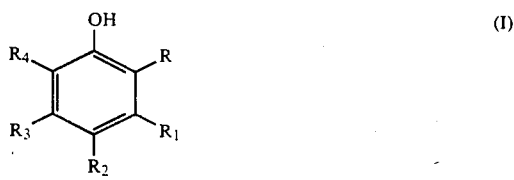

wherein R represents hydrogen, alkyl, alkoxy, aryl, halogen or hydroxy,
$R_1$ is hydrogen or alkyl,
$R_2$ can be hydrogen or hydroxy,
$R_3$ is hydrogen or alkyl,
$R_4$ represents hydrogen, alkyl, alkoxy, aryl, or halogen, or
R and $R_1$ and/or $R_3$ and $R_4$, when taken together, represent a butadienyl chain of formula

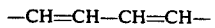

Which forms a condensed ring on the phenol, with the proviso that R can be a hydrogen atom only when $R_2$ is hydroxy, and with the further proviso that $R_4$ can be hydrogen only when one of R and $R_2$ is hydroxy.

For the purposes of the present invention, the term "alkyl" means a straight or branched chain alkyl radical containing from 1 to 6 carbon atoms, such as, e.g., methyl, ethyl, propyl, isopropyl, butyl, sec.butyl, tert.butyl, pentyl, hexyl, etc. and, analogously, the term "alkoxy" identifies a straight or branched chain alkoxy radical containing from 1 to 6 carbon atoms, such as, e.g., methoxy, ethoxy, isopropoxy, tert.butoxy, pentyloxy etc.. The term "aryl" indicates a phenyl radical, or a phenyl radical substituted with one or more groups independently selected from alkyl, alkoxy and halogen. Finally, the term "halogen" indicates any of chlorine, bromine, iodine and fluorine.

The process according to the present invention consists essentially in oxidating the phenol with $H_2O_2$ in the presence of a catalyst selected from bromine, iodine, hydrogen bromide and hydrogen iodide. The reaction is preferably carried out by using commercial aqueous solutions of $H_2O_2$. Hence, when as the starting phenol one which is soluble in water is used, it is not necessary to use any other solvents, whilst, when the starting phenol is insoluble, or only partially soluble, in water, it is necessary to use an organic solvent which is miscible with water for making it possible the reaction to occur in homogeneous phase. Suitable solvents for the intended purpose are all water-miscible organic solvents which are capable of dissolving the phenol, and do not interfere negatively with the course of the oxidation reaction. Such solvents are, e.g., the lower alkanols, typically methanol and ethanol, the organic acids, e.g., acetic acid, acetonitrile, etc.. In the oxidation of the 2,6-disubstituted mono-phenols, the molar ratio between $H_2O_2$ and the phenol is preferably higher than 2, and still more preferably it is from 2 to 3, whilst when diphenols are oxidated, such ratio is preferably from 1 to 2, and still more preferably from 1 to 1.5. Higher molar ratios can be used, but they do not afford any further advantages for the same reaction. The reaction is carried out at a temperature generally from 0° C. to the refluxing temperature of the reaction mixture and preferably, when mono-phenols are oxidated, at a temperature of from room temperature to the refluxing temperature of the reaction mixture, and, when the diphenols are oxidated, of from 0° C. to 60° C.

As to the catalyst, it was observed that, in the oxidation of the monophenols, a higher selectivity is obtained by using bromine or hydrogen bromide, and, still more preferably, bromine, rather than iodine or hydrogen iodide. In that case, very good results are obtained by using the catalyst, during the course of the reaction, at a molar concentration higher than 50% of the steady-state concentration of the mono-phenol. This situation can be accomplished both by reacting all of the reactants together and using a catalyst amount equal to at least 51% of the starting phenol, and, more conveniently, using a much lower catalyst amount, but gradually adding the phenol over a period of time, to the solution of the catalyst and hydrogen peroxide, in such a way that the steady-state concentration of the catalyst is always higher than 50% of the steady-state concentration of the phenol, due to the fact that the phenol reacts rapidly, and its concentration in the reaction medium remains always low, whilst the concentration of the catalyst remains substantially equal to its initial concentration.

In the oxidation of the diphenols, a better selectivity was observed on the contrary when iodine or hydrogen iodide, and still more preferably, iodine, is used as the catalyst. In this case, excellent results were obtained by using catalyst amounts of from 0.1 to 10% by mol relatively to the diphenol used as the starting product.

If in the process of the present invention iodine and bromine are used as catalysts, the reaction rate can be increased, is desired, by initially adding a strong acid, which can be identical to the hydrogen bromide or hydrogen iodide catalipt, but which can also be sulphuric acid. This addition does not alter the excellent selectivity of the process, but simply makes it faster. At the end of the oxidation reaction, the product is easily separated from the solution by crystallization, after optionally removing a portion of the solvent in a preliminary step. The process of the present invention leads to the corresponding quinone with high yields and with a high selectivity. This result appears more surprising on considering that under the same conditions, the other halogens or hydrogen halides either do not yield any results, or give rise to extremely low yields and selectivities. Advantages of the process of oxidation of the phenols according to the present invention are the low cost of the oxidating agent and the fact that the reduction product (water) does not present disposal problems; furthermore, the operative accomplishing thereof is extremely simple, which makes the methodology very versatile. The process of the present invention is disclosed in greater detail by the following examples. However, it should be understood that the present invention is not limited to these specific examples.

EXAMPLE 1

To a solution of 2,6-di-tert.butyl-phenol (11 g, 53.3 mmol), $H_2O_2$ at 59% (5 ml) and concentrated sulphuric acid (3 ml) in methanol (150 ml), bromine (1.5 ml) is added, and the so-obtained reaction mixture is refluxed for 10 minutes. The solution is then concentrated to a small volume (50 ml) and the product is crystallized out by cooling, with 99%-pure (GLC) 2,6-di-tert.butyl-1,4-benzoquinone (10.8 g, 92%) being obtained.

EXAMPLE 2

A solution of 2,6-di-tert.butyl-phenol (2.5 g, 12 mmol), concentrated sulphuric acid (3 ml), hydrogen peroxide at 60% (6 ml) and bromine (0.5 ml, 9.7 mmol) in methanol (50 ml) is refluxed, and to it a solution of 2,6-di-tert.butyl-phenol (8.5 g, 41.2 mmol) in methanol (100 ml) is added dropwise within a 40-minute time. On addition ended, the reaction mixture is refluxed for further 5 minutes, the solution is concentrated to small volume (50 ml) and 2,6-di-tert.butyl-1,4-benzoquinone (10.6 g, 90.4%) is crystallized.

EXAMPLE 3

A solution of 2,6-di-tert.butyl-phenol (11 g, 53.3 mmol), hydrogen peroxide at 60% (8 ml) and hydrogen bromide (5 g, 61.7 mmol) in methanol (150 ml) is refluxed for 25 minutes. On concentrating the solution, 2,6-di-tert.butyl-1,4-benzoquinone (10.5 g, 89.4%) crystallizes. This product is hydrogenated, in methanol (110 ml), in autoclave, with Pd/C at 5% (0.12 g), under a hydrogen pressure of 10 kg/cm$^2$, for 50 minutes, at 20° C. After the catalyst being filtered off, and solvent evaporation, 2,6-di-tert.butyl-hydroquinone is obtained with a yield of 97%.

EXAMPLE 4

A solution of hydrogen peroxide at 60% (7 ml), 2,6-di-tert.butyl-phenol (2.5 g, 12 mmol) and hydrogen bromide (1 g, 12.3 mmol) in methanol (50 ml) is refluxed. Into it a solution of 2,6-di-tert.butyl-phenol (8.5 g, 41.2 mmol) in methanol (100 ml) is then added dropwise within a 40 minute time. The reaction mixture is heated for further 5 minutes, the solution is concentrated and 2,6-di-tert.butyl-1,4-benzoquinone (10.6 g, 90.4%) is crystallized.

EXAMPLE 5

The process is carried out as in Example 1, but using 2,6-dimethyl-phenol instead of 2,6-di-tert.butyl-phenol, 2,6-dimethyl-1,4-benzoquinone being obtained with a yield of 85%.

EXAMPLE 6

The process is carried out as in Example 1, but using 2,3,6-trimethyl-phenol instead of 2,6-di-tert.butyl-phenol, 2,3,6-trimethyl-1,4-benzoquinone being obtained with a yield of 77%.

EXAMPLE 7

The process is carried out as in Example 1, but using 2-methyl-naphthol instead of 2,6-di-tert.butyl-phenol, 2-methyl-naphthoquinone being obtained with a yield of 94%.

EXAMPLES 8-17

General Methodology

A solution of a suitable diphenol (20 mmol) in methanol or acetic acid (60 ml) is treated 4 hours long with hydrogen peroxide at 60% (22 mmol), concentrated sulphuric acid (1 ml) and bromine or iodine or hydrogen iodide (1 mmol) at 25° C.

2,6-Di-tert.butyl-1,4-benzoquinone and 1,4-naphthoquinone crystallize directly out from the solution, whilst in the other cases the quinone is isolated by evaporating the solvent. The results obtained are reported in following Table 1:

TABLE 1

| Example No. | Diphenol | Catalyst | Yield, % |
|---|---|---|---|
| 8 | Hydroquinone | $I_2$ | 97 |
| 9 | Hydroquinone | $Br_2$ | 52 |
| 10 | 2,3,5-trimethylhydroquinone | $I_2$ | 100 |
| 11 | 2,3,5-trimethylhydroquinone | $Br_2$ | 74 |
| 12 | 1,4-dioxynaphthalene | $I_2$ | 100 |
| 13 | 1,4-dioxynaphthalene | $Br_2$ | 72 |
| 14 | 2,6-di-tert.butyl-hydroquinone | $I_2$ | 86 |
| 15 | 2,6-di-tert.butyl-hydroquinone | $Br_2$ | 68 |
| 16 | 3,5-di-tert.butyl-pyrocatechol | $I_2$ | 76 |
| 17 | 3,5-di-tert.butyl-pyrocatechol | $Br_2$ | 48 |

EXAMPLES 18–19

General Methodology

A solution of diphenol (20 mmol) in methanol (60 ml) is treated with hydrogen iodide (2 mmol) and hydrogen peroxide at 60% (24 mmol) for 4 hours. By evaporating the solvent, the corresponding quinones are obtained. The results are shown in following Table 2:

TABLE 2

| Example No. | Diphenol | Catalyst | Yield, % |
|---|---|---|---|
| 18 | Hydroquinone | HI | 98 |
| 19 | 1,4-dioxy-naphthalene | HI | 96 |

13 mmol of hydroquinone (or of its methylderivative) is added to 40 ml of water; 17 mmol of $H_2O_2$ at 30% and 1.3 mmol of HI are added, and the whole mass is kept stirred for 4 hours at room temperature.

The corresponding quinones, which contain only traces of the diphenols used as the starting product, precipitate out.

Trimethyl-benzoquinone separates initially in an oily state, but solidifies after cooling.

The following yields are obtained:

| Example | Diphenol | Yield |
|---|---|---|
| 20 | hydroquinone | 94% |
| 21 | 2-methyl-hydroquinone | 95% |
| 22 | 2,6-dimethyl-hydroquinone | 92% |
| 23 | 2,3,4-trimethyl-hydroquinone | 88% |

We claim:

1. A process for the synthesis of quinones consisting essentially of oxidizing a 2,6-di-substituted mono-phenol or a 2,6-di-substituted diphenol with $H_2O_2$ or $H_2O_2$ in an aqueous solution, in the presence of a catalytic amount of catalyst selected from the group consisting of bromine, iodine, hydrogen bromide and hydrogen iodide.

2. The process according to claim 1, wherein the mono-phenol or the di-phenol is represented by general formula (I):

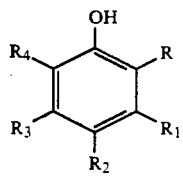

(I)

wherein R is hydrogen, an alkyl, an alkoxy, an aryl, a halogen or hydroxy, $R_1$ is hydrogen or an alkyl,
$R_2$ is hydrogen or hydroxy,
$R_3$ is hydrogen or an alkyl,
$R_4$ is hydrogen, an alkyl, an alkoxy, an aryl, or a halogen, and R and $R_1$ and/or $R_3$ and $R_4$, when taken together, represent a butadienyl chain of formula $$-CH=CH-CH=CH-$$

which forms a condensed ring on the mono-phenol or diphenol, with the proviso that R is hydrogen only when $R_2$ is hydroxy, and with the further proviso that $R_4$ is hydrogen only when one of R and $R_2$ is hydroxy.

3. The process according to claim 1, wherein the oxidation is carried out at a temperature of from 0° C. to the refluxing temperature of the oxidation mixture.

4. The process according to claim 1, wherein the mono-phenol or the diphenol is a 2,6-di-substituted mono-phenol.

5. The process according to claim 4, wherein the catalyst is selected from the group consisting of bromine and hydrogen bromide.

6. The process according to claim 5 wherein the catalyst is bromine.

7. The process according to claim 4, wherein hydrogen peroxide is used in such an amount that the molar ratio of hydrogen peroxide to the 2,6-di-substituted mono-phenol is higher than 2.

8. The process according to claim 7, wherein said ratio is from 2 to 3.

9. The process according to claim 4, wherein during the course of the oxidation, the molar concentration of the catalyst is higher than 50% of the steady-state concentration of the 2,6-di-substituted mono-phenol.

10. The process according to claim 8, wherein the temperature is of from room temperature to the refluxing temperature of the oxidation mixture.

11. The process according to claim 1, wherein the mono-phenol or the diphenol is a 2,6-di-substituted di-phenol.

12. The process according to claim 11, wherein the catalyst is selected from the group consisting of iodine and hydrogen iodide.

13. The process according to claim 12, wherein the catalyst is iodine.

14. The process according to claim 11, wherein hydrogen peroxide is used in such an amount that the molar ratio of hydrogen peroxide to the 2,6-di-substituted diphenol is from 1 to 2.

15. The process according to claim 14, wherein said ratio is from 1 to 1.5.

16. The process according to claim 11, wherein the catalyst is used in an amount of from 0.1 to 10% by mol relatively to the 2,6-di-substituted diphenol.

17. The process according to claim 11, wherein the temperature is of from 0° C. to 60° C.

18. The process according to claim 1, wherein the oxidation is carried out in the presence of a strong acid.

19. The process according to claim 18, wherein the strong acid is sulphuric acid.

20. A process for the synthesis of quinones consisting essentially of oxidizing a 2,6-di-substituted mono-phenol or a 2,6-di-substituted diphenol with $H_2O_2$ or $H_2O_2$ in an aqueous solution, in the presence of a catalytic amount of a catalyst selected from the group consisting of bromine, iodine, hydrogen bromide and hydrogen iodide, wherein the oxidation is carried out in the presence of a solvent selected from the group consisting of a lower alkanol and an organic acid.

21. The process according to claim 20, wherein the solvent is selected from the group consisting of lower alkanols and organic acids.

22. The process according to claim 20, wherein the solvent is selected from the group consisting of methanol, ethanol and acetic acid.

* * * * *

UNITED STATES PATENT AND TRADEMARK OFFICE
CERTIFICATE OF CORRECTION

PATENT NO. : 5,175,318
DATED : December 29, 1992
INVENTOR(S) : Francesco Minisci, et al It is certified that error appears in the above-indentified patent and that said Letters Patent is hereby corrected as shown below:

On the title page, item [73] Assignee: change "Della" to --Delle--.

Signed and Sealed this

Sixth Day of December, 1994

Attest:

BRUCE LEHMAN

*Attesting Officer*   *Commissioner of Patents and Trademarks*